United States Patent
Guillon et al.

(10) Patent No.: US 7,851,665 B2
(45) Date of Patent: Dec. 14, 2010

(54) CATALYST COMPRISING A ZEOLITE WITH STRUCTURE TYPE NES AND A ZEOLITE WITH STRUCTURE TYPE EUO, AND USE IN ISOMERIZING C8 AROMATIC COMPOUNDS

(75) Inventors: Emmanuelle Guillon, Vernaison (FR); Eric Sanchez, Saint Genis Laval (FR); Sylvie Lacombe, Saint Genis Laval (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 994 days.

(21) Appl. No.: 11/642,586

(22) Filed: Dec. 21, 2006

(65) Prior Publication Data

US 2007/0167660 A1    Jul. 19, 2007

(30) Foreign Application Priority Data

Dec. 22, 2005    (FR) .................................. 05 13157

(51) Int. Cl.
*C07C 5/27*    (2006.01)
(52) U.S. Cl. .................... 585/481; 585/482; 585/480
(58) Field of Classification Search ................ 585/480, 585/481, 482
See application file for complete search history.

(56) References Cited

U.S. PATENT DOCUMENTS

| 4,537,754 | A |   | 8/1985 | Casci et al. |
|-----------|---|---|--------|--------------|
| 5,446,234 | A | * | 8/1995 | Casci et al. ............... 585/467 |
| 6,057,486 | A |   | 5/2000 | Merlen et al. |
| 6,514,479 | B1 | * | 2/2003 | Merlen et al. ............... 423/705 |
| 2005/0215838 | A1 |   | 9/2005 | Negiz et al. |

FOREIGN PATENT DOCUMENTS

| EP | 0378916 A | 7/1990 |
|----|-----------|--------|
| EP | 0462745 A | 12/1991 |

* cited by examiner

*Primary Examiner*—Thuan Dinh Dang
(74) *Attorney, Agent, or Firm*—Millen, White, Zelano & Branigan, P.C.

(57) ABSTRACT

A catalyst is described comprising at least one zeolite with structure type EUO, at least one zeolite with structure type NES, at least one metal selected from metals from groups IIIA, VIIB, VIIB and VIII and at least one porous mineral matrix. The catalyst of the invention is used in a process for isomerizing a feed comprising aromatic compounds containing 8 carbon atoms per molecule.

24 Claims, No Drawings

CATALYST COMPRISING A ZEOLITE WITH STRUCTURE TYPE NES AND A ZEOLITE WITH STRUCTURE TYPE EUO, AND USE IN ISOMERIZING C8 AROMATIC COMPOUNDS

The present invention relates to a catalyst formed from at least two zeolites, one with structure type EUO and the other with structure type NES, for use, for example, in aromatic hydrocarbon transformation reactions. More precisely, it concerns a catalyst for the isomerization of C8 aromatic compounds. The present invention also concerns the use of said catalyst in a process for isomerizing a feed comprising aromatic compounds containing 8 carbon atoms per molecule.

PRIOR ART

In known processes for isomerizing aromatic compounds containing eight carbon atoms (AC8), a feed which is generally low in para-xylene with respect to the thermodynamic equilibrium of the mixture (i.e. with a para-xylene content which is substantially lower than that of a mixture at thermodynamic equilibrium at the temperature under consideration, that mixture comprising at least one compound selected from the group formed by meta-xylene, ortho-xylene, para-xylene and ethylbenzene) and generally rich in ethylbenzene with respect to that mixture at thermodynamic equilibrium is introduced into a reactor containing at least one catalyst under temperature and pressure conditions which are suitable for the production of a composition at the outlet from said reactor of aromatic compounds containing 8 carbon atoms which is as close as possible to the composition of said mixture at thermodynamic equilibrium at the temperature of the reactor. To obtain such a composition, the skilled person is generally constrained to maximize conversion of the ethylbenzene present in the feed. Xylene and possibly meta-xylene or ortho-xylene, which are the desired isomers as they are of great advantage especially in the synthetic fibre industry, are separated from the mixture obtained from the outlet from the isomerization reactor.

The catalysts used to carry out a process for isomerizing aromatic compounds containing 8 carbon atoms are generally zeolitic catalysts. Prior art catalysts, in particular catalysts based on mordenite zeolite, can only produce mediocre performances as they lead to non negligible side reactions which generate losses. An example of such secondary reactions which can be cited is the opening of naphthene rings which may or may not be followed by cracking (losses to paraffins) or disproportionation and transalkylation of aromatics containing 8 carbon atoms (losses to undesirable aromatic compounds) or hydrogenation of aromatic compounds (losses to naphthenes). Catalysts based on ZSM-5 zeolite, used alone or mixed with other zeolites such as mordenite, have already been used but also do not produce optimum performances. More recently, a catalyst has been proposed which is based on a zeolite with structure type EUO (EP-A1-0 923 987). Thus, the present invention proposes a novel catalyst having a composition such that when it is used to isomerize aromatic compounds containing 8 carbon atoms per molecule, the ethylbenzene conversion is improved and the secondary reactions are limited, reducing losses as a result.

SUMMARY

The present invention provides a catalyst comprising at least one zeolite with structure type NES, at least one zeolite with structure type EUO, at least one metal selected from metals from groups VIII, VIIB, VIIB and IIIA and at least one porous mineral matrix. Advantageously, the catalyst of the present invention also optionally comprises at least one metal selected from metals from group IVA. Each of the zeolites included in the catalyst of the invention contains silica and at least one element T selected from the group formed by aluminium, iron, gallium and boron, preferably aluminium.

The present invention also concerns the use of said catalyst in a process for isomerizing a feed comprising aromatic compounds containing 8 carbon atoms per molecule.

ADVANTAGE

It has surprisingly been discovered that a composite catalyst comprising a combination of at least one zeolite with structure type NES and at least one zeolite with structure type EUO and at least one metal selected from metals from groups IIIA, VIIB, VIIB and VIII results in improved catalytic performances in reactions for the isomerization of aromatic compounds containing 8 carbon atoms per molecule. In particular, the catalyst of the invention can produce a higher conversion of ethylbenzene than that produced with prior art catalysts, in particular catalysts based on a single zeolite with structure type EUO or a single zeolite with structure type MOR. Further, secondary reactions are substantially limited with the catalyst of the invention, thus generating fewer losses compared with prior art catalysts.

Further, by adjusting the relative quantity of the two zeolites, that with structure type EUO and that with structure type NES, in the catalyst of the invention, it is possible to treat a very wide range of mixtures of hydrocarbon feeds.

DESCRIPTION

The present invention provides a catalyst comprising at least one zeolite with structure type EUO, at least one zeolite with structure type NES, at least one metal selected from metals from groups IIIA, VIIB, VIIB and VIII and at least one porous mineral matrix.

The zeolite with structure type EUO and the zeolite with structure type NES present in the catalyst of the invention comprise silicon and at least one element T selected from the group formed by aluminium, iron, gallium and boron, preferably aluminium. They are preferably practically entirely in the acid form.

The zeolite with structure type EUO present in the catalyst of the invention has already been described in the art. It has a mono-dimensional microporous framework with a pore diameter of 4.1×5.7 Å (1 Å=1 Angstrom=$10^{-10}$ in) ("Atlas of zeolite framework types", W M Meier, D H Olson, Ch. Baerlocher, $5^{th}$ edition, 2001). Further, N A Briscoe et al disclosed, in an article in the review Zeolites (1988, 8, 74), that these mono-dimensional channels have lateral pockets with a depth of 8.1 Å and a diameter of 6.8×5.8 Å. The zeolite with structure type EUO covers zeolites EU-1 (EP-B1-0 042 226), ZSM-50 (U.S. Pat. No. 4,640,829) and TPZ-3 (EP-A1-0 051 318). The zeolite with structure type EUO present in the catalyst of the invention is preferably an EU-1 zeolite. Said zeolite with structure type EUO is characterized by a Si/T atomic ratio, preferably a Si/Al atomic ratio, of at least 5, advantageously in the range 5 to 100. Said zeolite with structure type EUO is at least in part, preferably almost completely in its acid form, i.e. in its hydrogen form $H^+$, the sodium content preferably being such that the atomic ratio Na/T is less than 0.1, more preferably less than 0.05. One mode for synthesizing an EU-1 zeolite is described in EP-B1-0 042 226. One mode for synthesizing a ZSM-50 zeolite is described in U.S. Pat. No. 4,640,829. One mode for synthesizing a TPZ-3 zeolite is described in EP-A1-0 051 318.

The zeolite with structure type NES included in the catalyst of the present invention is listed in the Atlas of Zeolites ("Atlas of zeolite framework types", W M Meier, D H Olson, Ch. Baerlocher, 5$^{th}$ edition, 2001). Preferably, it is a NU-87 zeolite. Said zeolite with structure type NES, preferably a NU-87 zeolite, is characterized by an Si/T atomic ratio, preferably a Si/Al atomic ratio, in the range 2 to 250, preferably in the range 5 to 150 and more preferably in the range 10 to 80. The zeolite with structure type NES, preferably a NU-87 zeolite, is preferably such that the element T, advantageously aluminium, has been extracted from the framework. The sodium content is less than 0.2% by weight, preferably less than 0.1% by weight and more preferably less than 0.05% by weight with respect to the total weight of dry zeolite. Said zeolite with structure type NES is synthesized using the methods described in the references cited in the Atlas of Zeolites or by any other method described in the literature available to the skilled person. In particular, a NU-87 zeolite may be prepared by mixing at least one source of silicon, at least one source of an element T selected from the group formed by aluminium, iron, gallium and boron, at least one alkali cation and at least one organic template selected from polymethylene diammonium salts, for example decamethonium bromide. A method for preparing a zeolite with structure type NES, preferably a NU-87 zeolite, is given in patents EP-0 377 291, EP-B1-0 378 916 and U.S. Pat. No. 5,041,402, the contents of each of these patents being hereby incorporated by reference.

The Si/T atomic ratios, preferably the Si/Al atomic ratios, of the zeolites with structure type NES and EUO described above are those obtained at the end of synthesis of said zeolites or obtained after post-synthesis treatments to extract a portion of the T atoms, termed dealumination treatments when T is aluminium, which are well known to the skilled person, non exhaustive examples thereof being hydrothermal treatments which may or may not be followed by acid attacks, or direct acid attacks with mineral or organic acid solutions to extract a portion of the T atoms, preferably a portion of the aluminium atoms from the zeolitic framework. Preferably, the zeolite with structure type NES present in the catalyst of the invention has been obtained by post synthesis dealumination.

The Si/T atomic ratio, preferably the Si/Al atomic ratio, of the zeolite with structure type EUO and the zeolite with structure type NES in the composition of the catalyst of the invention and the chemical composition of said catalyst are determined by X ray fluorescence and atomic absorption.

The zeolites with structure type NES and EUO in the composition of the catalyst of the invention may be calcined and exchanged by means of at least one treatment with a solution of at least one ammonium salt to obtain the ammonium form of the zeolites which, once calcined, produce the hydrogen form of said zeolites.

The zeolites with structure type NES and EUO in the composition of the catalyst of the invention are at least partially, preferably practically completely in the acid form, i.e. in the hydrogen form (H$^+$). The Na/T atomic ratio is generally less than 10%, preferably less than 5% and more preferably less than 1%.

Said catalyst of the invention also comprises at least one metal selected from metals from groups IIIA, VIIB, VIIB and VIII, preferably selected from metals from groups VIIB and VIII, and more preferably said metal is selected from metals from group VIII. Said metal is present in an amount in the range 0.01% to 5% by weight with respect to the total catalyst weight. Of the metals from group VIIB, rhenium is preferred. Of the metals from group VIII, platinum is preferred. Of the metals from group IIIA, gallium is preferred. Of the metals from group VIB, molybdenum is preferred. A preferred catalyst of the invention comprises at least one NU-87 zeolite, at least one EU-1 zeolite, at least platinum and at least one porous mineral matrix, for example alumina. A further preferred catalyst of the invention comprises at least one NU-87 zeolite, at least one EU-1 zeolite, at least platinum, at least rhenium and at least one porous mineral matrix, for example alumina. The catalyst of the invention optionally further comprises at least one additional metal selected from metals from group IVA, preferably tin. Said additional metal is preferably present in an amount in the range 0.01% to 5% by weight and more preferably in the range 0.5% to 3% by weight with respect to the total catalyst weight.

The porous mineral matrix, present in an amount by weight in the range 5% to 98%, preferably in the range 20% to 95%, more preferably in the range 30% to 92% with respect to the total catalyst weight, is generally selected from elements from the group formed by clays (for example from natural clays such as kaolin or bentonite), magnesia, aluminas, silicas, titanium oxide, boron oxide, zirconia, aluminium phosphates, titanium phosphates, zirconium phosphates, amorphous silica-aluminas and charcoal, preferably from elements from the group formed by aluminas and clays, more preferably from aluminas, in particular gamma alumina.

In a first variation of the preparation of the catalyst of the invention, prior to forming, at least one of the zeolites described above, i.e. at least one zeolite with structure type NES or at least one zeolite with structure type EUO, included in said catalyst undergoes deposition of at least one metal selected from metals from groups IIIA, VIIB, VIIB and VIII, and optionally deposition of at least one metal from group IVA. It is also possible that the zeolite with structure type NES could undergo deposition of a metal selected form metals from groups IIIA, VIIB, VIIB and VIII, preferably from metals from group VIIB, more preferably rhenium, and that the zeolite with structure type EUO undergoes deposition of another metal selected from metals from groups IIIA, VIIB, VIIB and VIII, preferably from metals from group VIII, more preferably platinum. The zeolites, one of which is charged with metal(s) and in the powdered state, are mixed using any powder mixing technique known to the skilled person.

Once the powdered zeolites, one of which is charged with metal(s) have been mixed, the mixture is formed using any technique known to the skilled person. In particular, it may be mixed with a porous mineral matrix, generally amorphous, for example a moist alumina gel powder. The mixture is then formed, for example by extrusion through a die. Forming may be carried out with matrices other than alumina, such as magnesia, amorphous silica-aluminas, natural clays (kaolin, bentonite, sepiolite, attapulgite), silica, titanium oxide, boron oxide, zirconia, aluminium phosphates, titanium phosphates, zirconium phosphates, charcoal and mixtures thereof. Preferably, matrices containing alumina are used, in any form known to the skilled person, and more preferably gamma alumina. Advantageously, mixtures of alumina and silica are used, as well as mixtures of alumina and silica-alumina. Techniques other than extrusion, such as pelletization or bowl granulation, may be used. after the forming step, the product obtained undergoes a drying step carried out at a temperature in the range 80° C. to 150° C. followed by a calcining step carried out at a temperature in the range 300° C. to 600° C., preferably in the range 400° C. to 550° C.

In a second variation for the preparation of the catalyst of the invention, at least one metal selected from metals from groups IIIA, VIIB, VIIB and VIII and possibly at least one metal selected from metals from group IVA is(are) deposited on the catalytic support after forming the metal-free zeolites with structure types NES and EUO, using any process known to the skilled person and allowing the metal or metals to be deposited on the catalytic support. The term "support" means the mixture of zeolites (free of metals) with at least one porous mineral matrix after forming, drying at a temperature in the range 80° C. to 150° C. and calcining at a temperature in the range 300° C. to 600° C., preferably in the range 400° C. to 550° C. Initially, the zeolites with structure type NES and EUO are in the powdered state, said zeolites being mixed using any powder mixing technique known to the skilled person. Once the powdered zeolites have been mixed, the mixture is formed using any technique known to the skilled person. In particular, it may be mixed with a porous mineral matrix, generally amorphous, for example a moist alumina gel powder. The mixture is then formed, for example by extrusion through a die. Forming may be carried out with matrices other than alumina, in particular a matrix selected from elements from the group described above in the present description. The catalyst support of the present invention generally comprises the following amounts of matrix and zeolites:

- 2% to 95% by weight, preferably 5% to 80% by weight, more preferably 8% to 70% by weight of zeolites with structure type NES and EUO;
- 5% to 98% by weight, preferably 20% to 95% by weight, more preferably 30% to 92% by weight of at least one porous amorphous or low crystallinity mineral matrix of the oxide type.

To deposit the metal(s) on at least one of the zeolites and/or on the catalytic support in the first or second preparation variation of the preparation of the catalyst of the invention, it is possible to use the competitive cationic exchange technique in which the competitor is preferably ammonium nitrate, the competition ratio between the competitor and the metallic precursor being at least about 5 and advantageously in the range 5 to 200. It is also possible to use the dry impregnation or co-precipitation technique.

Sources for the metals from group VIII which may be used are well known to the skilled person. As an example, nitrates, sulphates, phosphates, halides, for example chlorides, bromides and fluorides, carboxylates, for example acetates and carbonates, can be used. In the case of platinum, hexachloroplatinic acid or platinum tetramine chloride are preferably used. In the case of nickel, nickel nitrate $Ni(NO_3)_2$ is preferably used. Sources of the metals from group VIIB which may be used are also well known to the skilled person. In the case of rhenium, an ammonium perrhenate complex $(NH_4)ReO_4$ or perrhenic acid is used. Sources of metals from group IIIA which may be used are also well known to the skilled person. In the case of gallium, gallium nitrate $Ga(NO_3)_3$ is preferred. Sources of metals from group VIB which may be used are also well known to the skilled person. In the case of molybdenum, it is possible to use molybdic acids and their salts, in particular ammonium salts such as ammonium molybdate, ammonium heptamolybdate or phosphomolybdic acid. Preferably, ammonium heptamolybdate $(NH_4)_6Mo_7O_{24}$ is used. Deposition of the metal or metals from groups IIIA, VIIB, VIIB and VIII and optionally from group IVA is generally followed by calcining in air or oxygen, usually between 300° C. and 600° C. for 0.5 to 10 hours, preferably in the range 350° C. to 550° C. for 1 to 4 hours. Reduction in hydrogen may then be carried out, generally at a temperature in the range 300° C. to 600° C. for 1 to 10 hours, preferably between 350° C. and 550° C. for 2 to 5 hours.

In the first and second variation in the preparation of the catalyst of the invention, it is also possible to deposit the metal or metals not directly onto the zeolites, but onto the porous mineral matrix (for example the alumina binder) of the support, before or after the forming step, using anion exchange. An example which can be cited in the case of depositing platinum is the hexachloroplatinic complex $H_2PtCl_6$ and in the case of depositing rhenium, perrhenic acid $HReO_4$ can be used. In general after depositing metal, the catalyst undergoes calcining then is reduced in hydrogen, as indicated above.

In the case in which the catalyst contains a plurality of metals, these latter may be introduced either all in the same manner or using different techniques, before or after forming depending on the preparation variation for the catalyst which is used and in any order. In the case in which the technique used is ion exchange, a plurality of successive exchanges may be necessary to introduce the required quantities of metals.

Regardless of the preparation variation in preparing the catalyst of the invention, after calcining said catalyst, reduction in hydrogen may be carried out, generally at a temperature in the range 300° C. to 600° C., preferably in the range 350° C. to 550° C., for a period in the range 1 to 10 hours, preferably in the range 2 to 5 hours. Said reduction may take place ex situ or in situ as regards the location in which said catalyst is used in a given reaction.

The distribution between the two zeolites present in the catalyst of the invention is such that the amount of zeolite with structure type EUO may be from 1% to 99%, preferably 5% to 95% and more preferably 10% to 90% as a percentage by weight of the zeolite with structure type EUO with respect to the totality of the zeolites introduced into the catalyst. Similarly, the amount of zeolite with structure type NES varies from 1% to 99%, preferably 5% to 95% and more preferably 10% to 90%, as a percentage by weight of zeolite with structure type NES with respect to the totality of the zeolites introduced into the catalyst.

The catalyst of the present invention is formed into grains with different forms and dimensions. It is generally used in the form of cylindrical or polylobed extrudates such as bilobes, trilobes, polylobes with a straight or twisted form, but may be fabricated and used in the form of powder, pellets, tablets, rings, beads or wheels.

The catalyst of the present invention may optionally contain sulphur. In this case, the sulphur is introduced into the formed and calcined catalyst containing the element(s) cited above, either in situ before the catalytic reaction or ex situ. Sulphurization is carried out using any sulphurizing agent which is well known to the skilled person, such as dimethyl disulphide or hydrogen sulphide. The optional sulphurization is carried out after reduction. In the case of in situ sulphurization, reduction, if the catalyst has not been reduced in advance, is used after sulphurization. In the case of ex situ sulphurization, reduction is carried out followed by sulphurization.

The invention also pertains to the use of catalyst of the invention in hydrocarbon conversion processes. More precisely, the present invention concerns a process for isomerizing a feed comprising aromatic compounds containing 8 carbon atoms per molecule carried out in the presence of a catalyst of the invention.

Said feed comprises a mixture of xylenes and ethylbenzene. Preferably, said feed is free of naphthalene and more preferably it is free of naphthalene and aromatic compounds containing at least 11 carbon atoms per molecule. Said process is generally carried out using the following operating conditions:

a temperature in the range 300° C. to 500° C., preferably in the range 320° C. to 450° C. and more preferably in the range 340° C. to 430° C.;

a partial pressure of hydrogen in the range 0.3 to 1.5 MPa, preferably in the range 0.4 to 1.2 MPa and more preferably in the range 0.7 to 1.2 MPa;

a total pressure in the range 0.45 to 1.9 MPa, preferably in the range 0.6 to 1.5 MPa;

a supply space velocity, expressed in kilograms of feed introduced per kilogram of catalyst per hour, in the range 0.25 to 30 $h^{-1}$, preferably in the range 1 to 10 and more preferably in the range 2 to 6 $h^{-1}$.

The following examples illustrate the invention without in any way limiting its scope.

EXAMPLE 1

Preparation of Catalyst Based on a EU-1 Zeolite (Comparative)

The starting material used was an as synthesized EU-1 zeolite comprising the organic template, silicon and aluminium, having an overall Si/Al atomic ratio of 13.6, a sodium content with respect to the weight of dry EU-1 zeolite of about 1.5% by weight, corresponding to a Na/Al atomic ratio of 0.6. Said EU-1 zeolite initially underwent dry calcining at 550° C. in a stream of air for 6 hours. The solid obtained then underwent three ion exchanges in a 10N $NH_4NO_3$ solution at about 100° C. for 4 hours for each exchange. At the end of said treatments, the EU-1 zeolite in the $NH_4$ form had an overall Si/Al atomic ratio of 18.3, a sodium content with respect to the weight of dry EU-1 zeolite of 50 ppm, corresponding to a Na/Al atomic ratio of 0.003. The EU-1 zeolite was then formed by extrusion with an alumina gel to obtain, after drying and calcining in dry air, the support constituted by 1.4 mm diameter extrudates, which contain 15% by weight of EU-1 zeolite in the H form and 85% alumina.

The support obtained underwent anion exchange with hexachloroplatinic acid in the presence of a competing agent (hydrochloric acid) to introduce 0.3% by weight of platinum with respect to the weight of catalyst. The moist solid was dried at 120° C. for 12 hours and calcined in a stream of dry air at a temperature of 500° C. for one hour. Catalyst A obtained contained 15.0% by weight of EU-1 zeolite in the H form, 84.7% of alumina and 0.3% of platinum.

EXAMPLE 2

Preparation of a Catalyst Based on a NU-87 Zeolite (Comparative)

The NU-87 zeolite was synthesized as described in European patent EP-B-0 377 291 or EP-B-0 378 916. It had an overall Si/Al atomic ratio of 17.2, a sodium content of 1256 ppm by weight. Said NU-87 zeolite initially underwent dry calcining at 550° C. in a stream of air and nitrogen for 6 hours. The solid obtained then underwent ion exchange in a solution of 10N $NH_4NO_3$ at about 100° C. for 4 hours. The NU-87 zeolite then underwent a treatment with a 7N nitric acid solution at about 100° C. for 5 hours. The volume V of the nitric acid solution used (in ml) was 10 times the weight W of the dry NU-87 zeolite (V/W=10). This treatment with 7N nitric acid solution was carried out a second time under the same operating conditions. At the end of those treatments, the zeolite obtained was in the H form and had an overall Si/Al atomic ratio of 33.3 and a Na content of 10 ppm.

The NU-87 zeolite was then formed by extrusion with an alumina gel to obtain, after drying and calcining in dry air, the support constituted by 1.4 mm diameter extrudates, which contained 15% by weight of NU-87 zeolite in the H form and 85% of alumina.

The support obtained underwent anion exchange with hexachloroplatinic acid in the presence of a competing agent (hydrochloric acid) to introduced 0.3% by weight of platinum with respect to the weight of catalyst. The moist solid was then dried at 120° C. for 12 hours and calcined in a flow of dry air at a temperature of 500° C. for one hour. Catalyst B obtained contained 15.0% by weight of NU-87 zeolite in the H form, 84.7% of alumina and 0.3% of platinum.

EXAMPLE 3

Preparation of a Catalyst Based on a NU-87 Zeolite and an EU-1 Zeolite (In Accordance with the Invention)

The EU-1 zeolite was synthesized as described in Example 1. At the end of the synthesis step, the EU-1 zeolite was in the $NH_4$ form, it had an Si/Al atomic ratio of 18.3, and a sodium content with respect to the weight of dry EU-1 zeolite of 50 ppm by weight, corresponding to a Na/Al atomic ratio of 0.003.

The NU-87 zeolite was synthesized as described in Example 2. At the end of the synthesis step, the NU-87 zeolite was in the H form and had an Si/Al atomic ratio of 33.3 and a Na content of 10 ppm.

The EU-1 and NU-87 zeolites, which were in the powdered state, were mixed mechanically then formed by extrusion with an alumina gel to obtain, after drying at 120° C. overnight and calcining at 500° C. in dry air, a support which contained 15% by weight of EU-1 and NU-87 zeolites and 85% by weight of alumina.

The support obtained underwent anion exchange with hexachloroplatinic acid in the presence of a competing agent (hydrochloric acid) to deposit 0.3% by weight of platinum with respect to the weight of catalyst. The moist solid was then dried at 120° C. for 12 hours and calcined in a flow of dry air at 500° C. for one hour. Catalyst C was obtained containing, by weight, 8.0% of EU-1 zeolite in the hydrogen form, 7.0% by weight of NU-87 zeolite in the H form, 84.7% of alumina and 0.3% of platinum.

EXAMPLE 4

Preparation of a Catalyst Based on a NU-87 Zeolite and an EU-1 Zeolite (In Accordance with the Invention)

The EU-1 zeolite was synthesized as described in Example 1. At the end of the synthesis step, the EU-1 zeolite was in the $NH_4$ form, it had an Si/Al atomic ratio of 18.3 and a sodium content with respect to the weight of dry EU-1 zeolite of 50 ppm by weight, corresponding to a Na/Al atomic ratio of 0.003. The EU-1 zeolite underwent dry impregnation with a hexachloroplatinic acid solution to deposit 0.15% by weight of platinum with respect to the final catalyst weight. The moist solid was dried at 120° C. for 12 hours and calcined in a flow of dry air at 500° C. for 1 hour.

The NU-87 zeolite was synthesized as described in Example 2. At the end of the synthesis step, the NU-87 zeolite was in the H form and had an Si/Al atomic ratio of 33.3 and a Na content of 10 ppm. The NU-87 zeolite underwent dry impregnation with a solution of ammonium perrhenate to deposit 0.15% by weight of rhenium with respect to the final catalyst weight. The moist solid was then dried at 120° C. for 12 hours and calcined in a flow of dry air at 500° C. for 1 hour.

The EU-1 zeolite impregnated with platinum and the NU-87 zeolite impregnated with rhenium were mixed then formed by extrusion with an alumina gel to obtain, after drying at 120° C. overnight and calcining at 500° C. in dry air, catalyst D containing 8.0% by weight of EU-1 zeolite in the hydrogen form, 7.0% by weight of NU-87 zeolite in the H form, 84.7% of alumina, 0.15% by weight of platinum and 0.15% by weight of rhenium.

EXAMPLE 5

Preparation of a Catalyst Based on a EU-1 Zeolite and a ZSM-22 Zeolite (Comparative)

The EU-1 zeolite was synthesized in the same manner as described in Example 1. At the end of the synthesis step, the EU-1 zeolite was in the $NH_4$ form, it had an Si/Al atomic ratio of 18.3 and a sodium content with respect to the weight of dry EU-1 zeolite of 50 ppm, corresponding to a Na/Al atomic ratio of 0.003.

The ZSM-22 zeolite was synthesized as described in the article by B Marler published in Zeolites, 7, (1987), 2327. At the end of the synthesis step, the zsm22 zeolite was in the H form and had an Si/Al atomic ratio of 33 and a Na content of 86 ppm.

The EU-1 and ZSM-22 zeolites, which were in the powdered state, were mixed mechanically then formed by extrusion with an alumina gel to obtain, after drying overnight at 120° C. and calcining at 500° C. in dry air, a support which contained 15% by weight of EU-1 and zsm22 zeolites and 85% by weight of alumina.

The support obtained underwent anion exchange with hexachloroplatinic acid in the presence of a competing agent (hydrochloric acid) to deposit 0.3% by weight of platinum with respect to the weight of catalyst. The moist solid was dried at 120° C. for 12 hours and calcined in a flow of dry air at 500° C. for one hour. Catalyst E was obtained containing, by weight, 8.0% of EU-1 zeolite in the hydrogen form, 7.0% by weight of ZSM-22 zeolite in the H form, 84.7% of alumina and 0.3% of platinum.

The invention claimed is:

1. A process for isomerizing a feed comprising aromatic compounds containing 8 carbon atoms per molecule, carried out in the presence of a catalyst comprising a combination of zeolites consisting of at least one individual zeolite with structure type EUO in an amount of 10-90% by weight of the total zeolite, at least one zeolite with different structure type NES in an amount of 10-90% by weight of the total zeolite, at least one metal selected from the groups consisting of metals from groups IIIA, VIB, VIIB and VIII and at least one porous mineral matrix.

2. A process for isomerizing a feed comprising aromatic compounds containing 8 carbon atoms per molecule, carried out in the presence of a catalyst comprising a combination of zeolites consisting essentially of at least one individual zeolite with structure type EUO in an amount of 10-90% by weight of the total zeolite, at least one zeolite with different structure type NES in an amount of 10-90% by weight of the total zeolite, at least one metal selected from the groups consisting of metals from groups IIIA, VIIB, VIIB and VIII and at least one porous mineral matrix.

3. A process according to claim 2, in which the zeolite with structure type NES is a NU-87 zeolite.

4. A process according to claim 2, in which said at least one metal is selected from the group consisting of metals from groups VIIB and VIII.

5. A process according to claim 2, wherein the catalyst comprises at least one NU-87 zeolite, at least one EU-1 zeolite, at least platinum and at least one porous mineral matrix.

6. A process according to claim 2, wherein the catalyst comprises at least one NU-87 zeolite, at least one EU-1 zeolite, at least platinum, at least rhenium and at least one porous mineral matrix.

7. A process according to claim 2, wherein the catalyst comprises at least one additional metal selected from group IVA metals.

8. A process according to claim 7, in which said additional metal is tin.

9. A process according to claim 2, in which the catalyst comprises sulphur.

10. A process according to claim 2, in which the zeolite with structure type EUO is a EU-1 zeolite.

11. An isomerization process according to claim 2, in which said feed comprises a mixture of xylenes and ethylbenzene.

12. An isomerization process according to claim 2, which is carried out at a temperature in the range 300° C. to 500° C., with a partial pressure of hydrogen in the range 0.3 to 1.5 MPa, with a total pressure in the range 0.45 to 1.9 MPa and a supply space velocity, expressed in kilograms of feed introduced per kilogram of catalyst per hour, in the range 0.25 to 30 $h^{-1}$.

13. An isomerization process according to claim 11, which is carried out at a temperature in the range 300° C. to 500° C., with a partial pressure of hydrogen in the range 0.3 to 1.5 MPa, with a total pressure in the range 0.45 to 1.9 MPa and a supply space velocity, expressed in kilograms of feed introduced per kilogram of catalyst per hour, in the range 0.25 to 30 $h^{-1}$.

14. A process according to claim 11, in which the zeolite with structure type EUO is a EU-1 zeolite.

15. A process according to claim 11, in which the zeolite with structure type NES is a NU-87 zeolite.

16. A process according to claim 11, in which said metal selected from metals from groups IIIA, VIIB, VIIB and VIII is selected from the group consisting of metals from groups VIIB and VIII.

17. A process according to claim 11, wherein the catalyst comprises at least one NU-87 zeolite, at least one EU-1 zeolite, at least platinum and at least one porous mineral matrix.

18. A process according to claim 11, wherein the catalyst comprises at least one NU-87 zeolite, at least one EU-1 zeolite, at least platinum, at least rhenium and at least one porous mineral matrix.

19. A process according to claim 11, wherein the catalyst comprises at least one additional metal selected from group IVA metals.

20. A process according to claim 11, in which said additional metal is tin.

21. A process according to claim 11, in which the catalyst comprises sulphur.

22. A process according to claim 2, wherein said individual zeolites amount to about 100% of all zeolites.

23. A process according to claim 17, wherein the amounts by weight of the NU-87 and EU-1 zeolites are approximately equal.

24. A process according to claim 23, wherein the catalyst further comprises rhenium.

* * * * *